United States Patent
Ci

(10) Patent No.: US 10,709,158 B2
(45) Date of Patent: Jul. 14, 2020

(54) NUTRITIONAL COMPOSITION FOR NOURISHING HEART AND METHOD FOR PREPARING THE SAME

(71) Applicant: Zhonghua Ci, Beijing (CN)

(72) Inventor: Zhonghua Ci, Beijing (CN)

(*) Notice: Subject to any disclaimer, the term of this patent is extended or adjusted under 35 U.S.C. 154(b) by 291 days.

(21) Appl. No.: 15/958,928

(22) Filed: Apr. 20, 2018

(65) Prior Publication Data

US 2019/0159497 A1    May 30, 2019

(30) Foreign Application Priority Data

Nov. 30, 2017 (CN) .......................... 2017 1 1242617

(51) Int. Cl.
| | | |
|---|---|---|
| *A23L 33/105* | (2016.01) | |
| *A61K 36/899* | (2006.01) | |
| *A61K 36/48* | (2006.01) | |
| *A61K 36/8967* | (2006.01) | |
| *A61K 36/77* | (2006.01) | |

(52) U.S. Cl.
CPC ............ *A23L 33/105* (2016.08); *A61K 36/48* (2013.01); *A61K 36/77* (2013.01); *A61K 36/899* (2013.01); *A61K 36/8967* (2013.01); *A23V 2002/00* (2013.01); *A23V 2200/326* (2013.01); *A23V 2250/21* (2013.01); *A23V 2300/38* (2013.01)

(58) Field of Classification Search
CPC .. A61K 2300/00; A61K 36/185; A61K 36/48; A61K 36/484; A61K 36/67; A61K 36/68; A61K 35/646; A61K 35/644; A61K 36/47; A61K 38/38; A61K 9/0095; A61K 9/2018; A61K 31/4525; A61K 31/704; A61K 31/7048; A61K 38/1767; A61K 9/0019; A61K 9/0053; A61K 9/2013; A61K 9/2054; A61K 9/2068; A61K 2236/15; A61K 2236/39; A61K 2236/51; A61K 2800/28; A61K 2800/412; A61K 2800/884; A61K 8/0245; A61K 8/19; A61K 8/21; A61K 8/24; A61K 8/25; A61K 8/34; A61K 9/08; A61K 9/1617; A61K 9/1623; A61K 9/1652; A61K 9/1664; A61K 9/1682; A61K 9/2004; A61K 9/2009; A61K 36/77; A61K 36/8967; A61K 36/899; A61P 35/00; A61P 29/00; A23L 33/105; A61Q 11/00; A23V 2002/00; A23V 2200/326; A23V 2250/21; A23V 2300/38
See application file for complete search history.

(56) References Cited

U.S. PATENT DOCUMENTS

2015/0037389 A1* 2/2015 Ragot .................... A61K 36/74
424/439

* cited by examiner

*Primary Examiner* — Aaron J Kosar
(74) *Attorney, Agent, or Firm* — Cantor Colburn LLP

(57) ABSTRACT

The present disclosure discloses a nutritional composition for nourishing heart. The nutritional composition includes: 58-83 parts by weight of rice, 7-25 parts by weight of red beans, 5-16 parts by weight of lotus seeds, 2-7 parts by weight of *lilium brownii*, and 0.4-1.6 parts by weight of longan. The present disclosure, in view of the heart's characteristics that clearing away the heart fire and calming the nerves can ward off diseases and prolong life, and prevent premature aging, provides the prescription with the purpose of nourishing the blood and tranquillizing, is suitable to cooperate with staple foods for long-term consumption and easily accepted by people due to the good taste, and can achieve certain efficacies of nourishing the heart and tranquillizing.

20 Claims, 1 Drawing Sheet

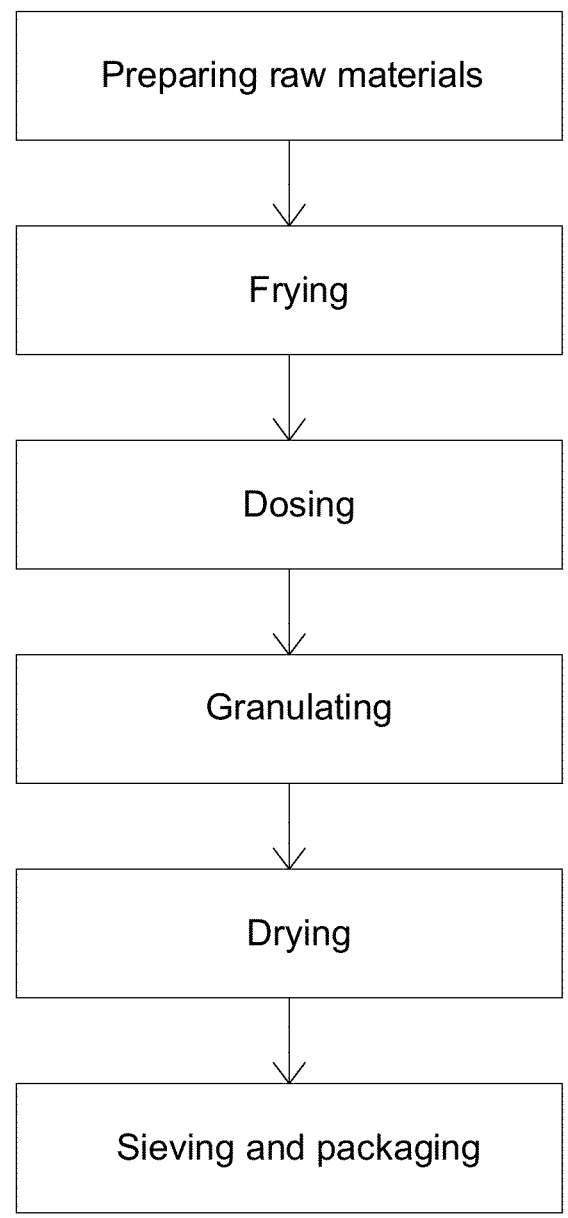

NUTRITIONAL COMPOSITION FOR NOURISHING HEART AND METHOD FOR PREPARING THE SAME

TECHNICAL FIELD

The present disclosure belongs to the technical field of food processing, and particularly relates to a nutritional composition for nourishing heart and a method for preparing the same.

BACKGROUND

Fast-pace and high-intensity work, deliberate competition, ceaseless stress, long-term metal strain and so on are heavy burdens for people in modern society. Moreover, when reaching middle ages, people's physiological functions decline, and many people develop syndromes of kidney deficiency in traditional Chinese medical science, such as palpitation, shortness of breath, tinnitus, dizziness, pale facial complexion, declined physical functions, cold extremities, mental fatigue, and sleeping disorder, all of which further form invisible metal stress, and seriously affect the life quality. According to the traditional Chinese medical science *Inner Canon of the Yellow Emperor*, "the heart governs the blood and vessels", "the vessels are the house of the blood", "all the blood is affiliated to the heart". The heart governs the blood, and the blood circulates in the vessels. The heart and the vessels are closely associated. The vessels are channels for the blood circulation, and the heat has the function of promoting the circulation of the blood in the vessels so as to nourish the whole body. This function is realized through the effect of the heart qi (vital energy). The ups and downs of the heart qi can be reflected by changes of blood vessels, therefore, it is stated in *Inner Canon of the Yellow Emperor* that "the heart cooperates with the blood vessels, the essence of which is reflected from the facial color". If the heart qi is vigorous, and the blood vessels are filled up, then the pulse is gentle and powerful. If the heart qi is insufficient, and the heart blood is deficient, then the pulse is thin and weak or irregular. If the heart blood is obstructed, then the pulse is unsmooth or intermittent. In the traditional medicines of more than 5000 years of the Chinese nation, some natural plant drugs indeed have curative effects in repairing and improving the heart functions. The invaluable experience, handed down from generation to generation, upon continuous application, development, and perfection of medical experts and health experts of successive dynasties, has become a type of unique natural plant drug (Chinese herbal medicine for nourishing the heart) with the efficacy of nourishing the heart. However, every medicine has its side effect, and long-term consumption of a lot of Chinese herbal medicine inevitably will cause damages to other aspects of the body.

On the basis of dietotherapy regimen of the traditional Chinese medical science (medicine and food share a common origin), more and more dieticians reasonably match food materials sharing a common origin of medicine and food, and achieve the object of nourishing the heart and tranquillizing through the function of channel tropism of the food materials' four natures and five tastes.

Currently, similar health-care foods with the function of nourishing the heart are already available in the market, but in most cases, the matching of different foods is chaotic, does not follow the pharmacology, and has relatively bad taste.

SUMMARY

A main object of the present disclosure is to provide a life nourishing and health protecting food product for nourishing heart and tranquillizing.

In order to achieve the above object, according to one aspect of the present disclosure, a nutritional composition for nourishing heart is provided.

The nutritional composition for nourishing heart according to the present disclosure includes: 58-83 parts by weight of rice, 7-25 parts by weight of red beans, 5-16 parts by weight of lotus seeds, 2-7 parts by weight of *lilium brownii*, and 0.4-1.6 parts by weight of longan.

Furthermore, the nutritional composition for nourishing heart includes the following components of raw materials in parts by weight: 65-75 parts by weight of rice, 11-18 parts by weight of red beans, 8-13 parts by weight of lotus seeds, 3-5 parts by weight of *lilium brownii*, and 0.7-1.2 parts by weight of longan.

Furthermore, the nutritional composition for nourishing heart includes: 70 parts by weight of rice, 15 parts by weight of red beans, 10 parts by weight of lotus seeds, 4 parts by weight of *lilium brownii*, and 1 part by weight of longan.

Furthermore, the nutritional composition for nourishing heart further includes 1-3 parts of a Chinese herbal medicine extract, wherein the Chinese herbal medicine extract includes: 12-30 parts by weight of mulberry, 5-15 parts by weight of ginkgo, 15-20 parts by weight of gorgon euryale seeds, 14-23 parts by weight of Chinese yam, 13-25 parts by weight of semen *sesami nigrum*, and 7-17 parts by weight of orange peels.

In order to achieve the above object, according to another aspect of the present disclosure, a method for processing a nutritional composition for nourishing heart is further provided.

The method for processing a nutritional composition for nourishing heart according to the present disclosure includes the following steps in sequence:

step 1, preparation of raw materials: subjecting rice, red beans, lotus seeds, *lilium brownii*, and longan to impurity removal and sorting for subsequent use;

step 2, frying: frying respective components of raw materials under a condition of 100-200° C. for 25-120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains;

step 5: drying: drying the mixed rice grains through a microwave dryer, wherein a water content of the material is kept below 12%, and cooling the dried mixed rice grains at a room temperature;

step 6: sieving and packaging: sieving the cooled mixed rice grains, and vacuum-packaging the sieved mixed rice grains.

Furthermore, temperatures of three phases of the double-screw extruder are kept at 60° C., 90-120° C., and 90° C., respectively.

Furthermore, a heating temperature of the microwave dryer is kept at 50-60° C.

Furthermore, in a dosing process of the step 3, 1-3 parts of a Chinese herbal medicine extract is further added, and the Chinese herbal medicine extract includes: 12-30 parts by weight of mulberry, 5-15 parts by weight of ginkgo, 15-20 parts by weight of gorgon euryale seeds, 14-23 parts by weight of Chinese yam, 13-25 parts by weight of semen *sesami nigrum*, and 7-17 parts by weight of orange peels.

Furthermore, the Chinese herbal medicine extract is prepared through the following method:

drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract.

Furthermore, in a process of preparing the Chinese herbal medicine extract, a vacuum dryer is used for drying, with a temperature of 75° C.-80° C., and a vacuum degree of between a negative pressure of 0.08 MPa and a negative pressure of 0.1 MPa.

The present disclosure, in view of the heart's characteristics that clearing away the heart fire and calming the nerves can ward off diseases and prolong life, and prevent premature aging, provides the prescription with the purpose of nourishing the blood and tranquillizing, is suitable to cooperate with staple foods for long-term consumption and easily accepted by people due to the good taste, and can achieve certain efficacies of nourishing the heart and tranquillizing.

BRIEF DESCRIPTION OF DRAWINGS

The accompanying drawing, which constitutes a part of the present application, is used to provide a further understanding of the present disclosure, so that other features, objects, and advantages of the present application become more obvious. The illustrative drawing for examples of the present disclosure and the description thereof are used to explain the present disclosure, rather than constitute an improper limitation on the present disclosure. In the drawing, FIG. 1 is a flow chart of a technology for processing a nutritional composition according to an example.

DETAILED DESCRIPTION OF EMBODIMENTS

In order to enable a person skilled in the art to better understand the solutions of the present invention, the technical solutions of the examples of the present invention will be described clearly and completely below with reference to the drawings of the examples of the present invention. Apparently, the examples described are some of the examples of the present invention, rather than all of the examples. All the other examples that are obtained by a person skilled in the art without inventive effort on the basis of the examples of the present invention shall be covered by the protection scope of the present invention.

In addition, the term "comprise" and any variant thereof are intended to cover non-exclusive inclusion, for example, a product comprising a series of raw materials or a method comprising a series of steps is not necessarily limited to the raw materials or the steps listed clearly, but can include other steps or raw materials that are not clearly listed or are inherent to the method and product.

It should be noted that the examples of the present invention and the features of the examples can be combined with each other if there is no conflict. The present invention will be described in detail below with reference to the accompanying drawings and examples.

A main object of the present disclosure is to provide a life nourishing and health protecting food product for nourishing heart and tranquillizing.

In one aspect, the present disclosure provides a nutritional composition for nourishing heart having such function, including: 58-83 parts by weight of rice, 7-25 parts by weight of red beans, 5-16 parts by weight of lotus seeds, 2-7 parts by weight of *lilium brownii*, and 0.4-1.6 parts by weight of longan.

The traditional Chinese medical science holds that rice is sweet in flavor and neutral in nature, acts on the spleen, stomach, and lung, has the efficacies of nourishing the middle energizer and supplementing qi, tonifying the spleen and nourishing the stomach, replenishing the essence and improving the memory, harmonizing the internal organs, promoting the blood circulation, improving the hearing and eyesight, eliminating annoyance, quenching thirst, and curing diarrhea, and it is believed that taking more rice can "strengthen the body and improve the look".

Red beans are sweet and sour in flavor and neutral in nature, act on the heart and small intestine, moisten dryness and relieve swelling, clear away toxic materials and discharge pus, and are used for edema abdominal fullness, beriberi edema, heat toxin carbuncle, mumps, erysipelas, and damp-heat jaundice.

Lotus seeds are sweet and astringent in flavor and neutral in nature, act on the spleen, kidney and heart, tonify the spleen and cures diarrhea, arrest morbid leukorrhea, tonify kidney and arrest seminal emission, nourish the heart and calm the nerves, and are used for spleen-deficiency diarrhea, morbid leukorrhea, gonobolia, and palpitation and insomnia.

*Lilium brownii* is sweet in flavor and cold in nature, acts on heart and lung, nourishes yin, moistens the lung, clears away the heart fire and tranquillizes, and is used for yin deficiency and irritating dry cough, over-strained cough, hemoptysis, dysphoria, pavor, insomnia and dreamful sleep, and trance.

Longan is sweet in flavor and warm in nature, acts on heart and spleen, invigorates heart and spleen, and nourishes the blood and tranquilizes, and is used for insomnia, amnesia, palpitation, chronic hemorrhage, menometrorrhagia, deficiency of qi and blood, and consumptive weakness and so on.

The nutritional composition for nourishing heart of the present disclosure achieves a perfect combination of dietotherapy and medical therapy by scientifically matching the theory that medicine and food share a common origin in combination with reasonable traditional Chinese medicines, reflecting the traditional preparing characteristics of the Chinese herbal medicine and providing the prescription based on the theory of the traditional Chinese medical science, and further enriching the purposes of the nutritional composition for nourishing heart, i.e. regulation, balancing, supplementation, and keeping fit. It has the main efficacy of nourishing the heart. The above composition can be taken as daily regulation diet.

On the basis of the above examples, the nutritional composition for nourishing heart further includes 1-3 parts by weight a Chinese herbal medicine extract, wherein the Chinese herbal medicine extract includes: 12-30 parts by weight of mulberry, 5-15 parts by weight of ginkgo, 15-20 parts by weight of gorgon euryale seeds, 14-23 parts by weight of Chinese yam, 13-25 parts by weight of semen *sesami nigrum*, and 7-17 parts by weight of orange peels.

Mulberry is cold in nature, and bitter and sour in flavor, acts on the heart, liver, and kidney, replenishes the blood and nourishes yin, generates the body fluid and moistens dryness, and is used for vertigo and tinnitus, palpitation and insomnia, premature graying of hair, constipation, body fluid deficiency and thirst, internal heat and consumptive thirst, blood deficiency constipation, liver and kidney tonification, calming down endogenous wind, essential fluid nourishment, and liver-kidney yin deficiency.

Ginkgo is sweet, bitter, and astringent in flavor, neutral in nature, and slightly toxic, acts on the lung, astringes the lung, relieves asthma, promotes astriction, and arrests morbid leukorrhea, and is used for asthma with abundant phlegm, morbid leukorrhea, gonorrhea, and enuresis and frequent urination.

Gorgon euryale seeds are sweet and astringent in flavor, and neutral in nature, act on the spleen and kidney, tonify kidney and strengthen essence, nourish spleen and cure diarrhea, dispel dampness, and arrest morbid leukorrhea, and are used for gonobolia and spermatorrhea, enuresis and frequent urination, lung-deficiency chronic diarrhea, gonorrhea, and morbid leukorrhea.

Chinese yam is sweet in flavor and neutral in nature, acts on spleen, lung and kidney, tonifies spleen and nourishes stomach, generates body fluid and tonifies lung, and tonifies kidney and arrests seminal emission; and is used for spleen deficiency, chronic diarrhea, lung deficiency, kidney deficiency, morbid leukorrhea and frequent urination.

Semen *sesami nigrum* is neutral in nature and sweet in flavor, acts on liver, lung, and kidney, nourishes liver and kidney, generates the body fluid, lubricates bowel, moistens skin, nurses hair, and improves eyesight.

Orange peels are acrid and slightly bitter in flavor and warm in nature, act on spleen and lung, have the efficacies of regulating qi and regulating middle energizer, and drying dampness and resolving phlegm, and can be used for the treatment of spleen and stomach qi stagnation, abdominal fullness and distention, vomiting, or chest stuffiness, anorexia and loose stool caused by dampness turbidity blocking, however, people having yin and body fluid depletion and having endogenous excess-heat should use them with caution.

In the Chinese herbal medicine composition, the above ingredients are combined so that efficacies of the various drugs generate a synergistic effect, with the functions of regulating yin and yang and balancing qi and blood, and can be used for keeping the balanced constitution, so that people are vigorous with strong resistibility, and avoid the occurrence of diseases. Moreover, the usage amount of the Chinese herbal medicine extract is relatively small, then it will not destroy the nutritional structure of the original nutritional composition for nourishing heart, and will not produce an undesirable flavor.

As shown in FIG. 1, a method for preparing the nutritional composition for nourishing heart includes the following steps in sequence:

step 1, preparation of raw materials: subjecting rice, red beans, lotus seeds, *lilium brownii*, and longan to impurity removal and sorting for subsequent use, wherein the raw materials are strictly checked, and impurities and soils are removed, effectively reducing the remnant of pollutants such as heavy metals and pesticides;

step 2, frying: frying respective components of raw materials under a condition of 100-200° C. for 25-120 min, wherein the temperature should not be too high to make the starchy food produce acrylamide, thus preventing loss of nutrients;

step 3, dosing: grinding the respective fried raw materials, then mixing and stirring evenly the respective ground raw materials according to proportions to obtain a rice powder, wherein the proportions of the respective raw materials are based on the prescription of the nutritional composition for nourishing heart of the present disclosure, and in the dosing process, 1-3 parts of a Chinese herbal medicine extract is further added, and the Chinese herbal medicine extract includes: 12-30 parts by weight of mulberry, 5-15 parts by weight of ginkgo, 15-20 parts by weight of gorgon euryale seeds, 14-23 parts by weight of Chinese yam, 13-25 parts by weight of semen *sesami nigrum*, and 7-17 parts by weight of orange peels. Specifically, the Chinese herbal medicine extract can be prepared through the following method: drying and grinding respective raw materials into a medicinal powder, subjecting the medicinal powder to ultrasonic extraction, centrifugation, and concentration with an ethanol solution of 40-65% in volume percentage to obtain the Chinese herbal medicine extract. In a process of preparing the Chinese herbal medicine extract, a vacuum dryer is used for drying, with a a temperature of 75° C.-80° C., and a vacuum degree of between a negative pressure of 0.08 MPa and a negative pressure of 0.1 MPa;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90-120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50-60° C.;

step 6: sieving and packaging: sieving the cooled mixed rice grains, and vacuum-packaging the sieved mixed rice grains, wherein by means of sieving, it is possible to improve the appearance and uniformity of the product particles. In practice, after the completion of the packaging, it is feasible to make a record and tag the product to indicate the product name, the lot number, the specification, the net weight, the production date, the post name and the responsible person, fill in the equipment receipt, and transfer the product into an intermediate station.

Example 1

A nutritional composition for nourishing heart includes: 58 parts by weight of rice, 7 parts by weight of red beans, 5 parts by weight of lotus seeds, 2 parts by weight of *lilium brownii*, and 0.4 parts by weight of longan.

A preparation method is as follows:

step 1, preparation of raw materials: subjecting rice, red beans, lotus seeds, *lilium brownii*, and longan to impurity removal and sorting for subsequent use;

step 2, frying: frying respective components of raw materials under a condition of 100° C. for 120 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 90° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 50° C.;

step 6: sieving and packaging: sieving the cooled mixed rice grains, and vacuum-packaging the sieved mixed rice grains.

Example 2

A nutritional composition for nourishing heart includes the following components of raw materials in parts by weight: 83 parts by weight of rice, 25 parts by weight of red beans, 16 parts by weight of lotus seeds, 7 parts by weight of *lilium brownii*, and 1.6 parts by weight of longan.

A preparation method is as follows:

step 1, preparation of raw materials: subjecting rice, red beans, lotus seeds, *lilium brownii*, and longan to impurity removal and sorting for subsequent use;

step 2, frying: frying respective components of raw materials under a condition of 200° C. for 25 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 120° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 60° C.;

step 6: sieving and packaging: sieving the cooled mixed rice grains, and vacuum-packaging the sieved mixed rice grains.

Example 3

A nutritional composition for nourishing heart includes the following components of raw materials in parts by weight: 65 parts by weight of rice, 11 parts by weight of red beans, 8 parts by weight of lotus seeds, 3 parts by weight of *lilium brownii*, and 0.7 parts by weight of longan.

A preparation method is as follows:

step 1, preparation of raw materials: subjecting rice, red beans, lotus seeds, *lilium brownii*, and longan to impurity removal and sorting for subsequent use;

step 2, frying: frying respective components of raw materials under a condition of 120° C. for 80 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 100° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 58° C.;

step 6: sieving and packaging: sieving the cooled mixed rice grains, and vacuum-packaging the sieved mixed rice grains.

Example 4

A nutritional composition for nourishing heart includes the following components of raw materials in parts by weight: 75 parts by weight of rice, 18 parts by weight of red beans, 13 parts by weight of lotus seeds, 5 parts by weight of *lilium brownii*, and 1.2 parts by weight of longan.

A preparation method is as follows:

step 1, preparation of raw materials: subjecting rice, red beans, lotus seeds, *lilium brownii*, and longan to impurity removal and sorting for subsequent use;

step 2, frying: frying respective components of raw materials under a condition of 130° C. for 60 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 105° C., and 90° C., respectively;

step 5: drying: drying the mixed rice grains through a microwave dryer, wherein a water content of the material is kept below 12%, cooling the dried mixed rice grains at a room temperature, wherein a heating temperature of the microwave dryer is kept at 53° C.;

step 6: sieving and packaging: sieving the cooled mixed rice grains, and vacuum-packaging the sieved mixed rice grains.

Example 5

A nutritional composition for nourishing heart includes the following components of raw materials in parts by weight: 70 parts by weight of rice, 15 parts by weight of red beans, 10 parts by weight of lotus seeds, 4 parts by weight of *lilium brownii*, and 1 part by weight of longan.

A preparation method is as follows:

step 1, preparation of raw materials: subjecting rice, red beans, lotus seeds, *lilium brownii*, and longan to impurity removal and sorting for subsequent use;

step 2, frying: frying respective components of raw materials under a condition of 150° C. for 40 min;

step 3, dosing: grinding the respective fried raw materials, then mixing and stirring evenly the respective ground raw materials according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 6

A nutritional composition for nourishing heart includes: 70 parts by weight of rice, 15 parts by weight of red beans, 10 parts by weight of lotus seeds, 4 parts by weight of *lilium brownii*, 1 part by weight of longan and 1 part by weight of a Chinese herbal medicine extract. The Chinese herbal medicine extract includes: 12 parts by weight of mulberry, 5 parts by weight of ginkgo, euryale seed 15 parts by weight of gorgon, 14 parts by weight of Chinese yam, 13 parts by weight of semen *sesami nigrum*, and 7 parts by weight of orange peels. The Chinese herbal medicine extract is prepared through the following method: drying and grinding respective raw materials into a medicinal powder, subjecting the medicinal powder to ultrasonic extraction, centrifugation, and concentration with an ethanol solution of 65% in volume percentage to obtain the Chinese herbal medicine extract. In a process of preparing the Chinese herbal medicine extract, a vacuum dryer is used for drying, with a temperature of 75° C., and a vacuum degree of a negative pressure of 0.08 MPa.

A method for preparing the nutritional composition for nourishing heart is as follows:

step 1, preparation of raw materials: subjecting rice, red beans, lotus seeds, *lilium brownii*, and longan to impurity removal and sorting for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Example 7

A nutritional composition for nourishing heart includes: 70 parts by weight of rice, 15 parts by weight of red beans, 10 parts by weight of lotus seeds, 4 parts by weight of *lilium brownii*, 1 part by weight of longan, and a Chinese herbal medicine extract 1. The Chinese herbal medicine extract includes: 30 parts by weight of mulberry, 15 parts by weight of ginkgo, 20 parts by weight of gorgon euryale seeds, 23 parts by weight of Chinese yam, 25 parts by weight of semen *sesami nigrum*, and 17 parts by weight of orange peels. The Chinese herbal medicine extract is prepared through the following method: drying and grinding respective raw materials into a medicinal powder, subjecting the medicinal powder to ultrasonic extraction, centrifugation, and concentration with an ethanol solution of 40% in volume percentage to obtain the Chinese herbal medicine extract. In a process of preparing the Chinese herbal medicine extract, a vacuum dryer is used for drying, with a temperature of 80° C., and a vacuum degree of a negative pressure of 0.1 MPa.

A method for preparing the nutritional composition for nourishing heart is as follows:

step 1, preparation of raw materials: subjecting rice, red beans, lotus seeds, *lilium brownii*, and longan to impurity removal and sorting for subsequent use;

step 2, frying: frying respective components of raw materials treated in step 1 under a condition of 150° C. for 40 min;

step 3, dosing: grinding the respective fried raw materials, then mixing and stirring evenly the respective ground raw materials with the Chinese herbal medicine extract according to proportions to obtain a rice powder;

step 4, granulating: extruding the rice powder obtained in step 3 through a double-screw extruder, followed by gelatinization and granulation, to obtain mixed rice grains, wherein temperatures of three phases of the double-screw extruder are kept at 60° C., 110° C., and 90° C., respectively;

step 5: drying: drying the mixed rice grains through a microwave dryer, wherein a water content of the material is kept below 12%, and cooling the dried mixed rice grains at a room temperature, wherein a heating temperature of the microwave dryer is kept at 55° C.;

step 6: sieving and packaging: sieving the cooled mixed rice grains, and vacuum-packaging the sieved mixed rice grains.

Experiment Example 1: Sensory Evaluation of Eating Quality

Evaluating method: scoring is made in comparison with reference samples according to the odor, appearance structure, palatability, taste, and texture of cold steamed rice. An overall score is a sum of respective items. Scoring rules are shown in Table 1. Products used for the sensory evaluation of this experiment example are staple foods, numbered as products 1 to 7, obtained by mixing the nutritional compositions for nourishing heart obtained in Examples 1 to 7 of the present disclosure with rice, respectively, a mixing ratio of rice to the nutritional composition for nourishing heart being 4:1. Statistical results of the evaluation scores corresponding to the products 1 to 7 are shown in Table 2.

An overall score of less than 50 indicates "very bad", 51-60 "bad", 61-70 "ordinary", 71-80 "relatively good", 81-90 "good", and more than 90 "excellent".

Uncovered matters such as specific operation steps, preparation work, evaluator determination, sample approval, instrument, and appliance should comply with GB/T 15682-2008 Inspection of Grain and Oils-Method for Sensory Evaluation of Paddy or Rice Cooking and Eating Quality.

TABLE 1

Scoring Rules for Sensory Evaluation of Steamed Rice

| First-grade Index Score | Second-grade Index Score | Description of specific properties: score |
|---|---|---|
| Odor 20 | Authenticity and Intensity 20 | Having unique aroma of steamed rice, rich in fragrance: 18~20 |
| | | Having unique aroma of steamed rice, delicate in fragrance of steamed rice: 15~17 |
| | | Having unique aroma of steamed rice, but not obvious in fragrance: 12~14 |
| | | Having no fragrance, but without undesirable odor: 7~12 |
| | | Having an undesirable odor: 0~6 |
| Appearance Structure 20 | Color 7 | Bright in color: 6~7 |
| | | Normal in color: 4~5 |
| | | Dull in color: 0~3 |
| | Gloss | Having obvious gloss: 7~8 |

TABLE 1-continued

Scoring Rules for Sensory Evaluation of Steamed Rice

| First-grade Index Score | Second-grade Index Score | Description of specific properties: score |
|---|---|---|
| | 8 | Slightly glossy: 5~6 |
| | | Having no gloss: 0~4 |
| | Integrity of Steamed Rice Grain | Compact steamed rice structure, good integrity of steamed rice grain: 4~5 |
| | 5 | Most of the steamed rice having a compact and complete structure: 3 |
| | | Some steamed rice grains explode: 0~2 |
| Palatability 30 | Viscosity 10 | Smooth, Viscous, not sticky to teeth: 8~10 |
| | | Viscous, basically not sticky to teeth: 6~7 |
| | | Viscous, sticky to teeth; or not viscous: 0~5 |
| | Elasticity 10 | Chewy: 8~10 |
| | | Slightly shewy: 6~7 |
| | | Loose, hard, feeling foreign matters present: 0~5 |
| | Hardness 10 | Neither too hard nor too soft: 8~10 |
| | | Slightly hard or slightly soft: 6~7 |
| | | Very hard or very soft: 0~5 |
| Taste 25 | Authenticity and Persistence 25 | Having relatively strong fragrance and sweet taste when chewed: 22~25 |
| | | Having light fragrance and sweet taste when chewed: 18~21 |
| | | Having no fragrance or sweet taste when chewed, but without undesirable odor: 16~17 |
| | | Having no fragrance or sweet taste when chewed, but having an undesirable odor: 0~15 |
| Texture of Cold Steamed Rice 5 | Agglomeration, Viscoelasticity, and Hardness 5 | Relatively loose, relatively good in viscoelasticity, moderate in hardness: 4~5 |
| | | Agglomerated, slightly bad in viscoelasticity, slightly hardened: 2~3 |
| | | Hardened, bad in viscoelasticity, and more rigid: 0~1 |

TABLE 2

Table of Statistical Results of Evaluation Scores of Respective Products

| Group | Overall Scoring/Score | Evaluation Result |
|---|---|---|
| Product 1 | 93 | Excellent |
| Product 2 | 96 | Excellent |
| Product 3 | 94 | Excellent |
| Product 4 | 93 | Excellent |
| Product 5 | 87 | Good |
| Product 6 | 90 | Excellent |
| Product 7 | 86 | Good |

It can be seen from the above test results that all the sensory evaluation results made by respective sensory evaluators on the nutritional compositions for nourishing heart prepared in Examples 1 to 7 in conjunction with rice are "excellent" and "good". It is indicated that the products of the present disclosure have relatively excellent performances in odor, appearance structure, palatability, taste, and texture of cold steamed rice.

Experiment Example 2: Influence on Sleeping Time of Mice

Experiment Materials:
1. Animals: SPF ICR mice, half of them being male and half of them being female, with a body weight of 18-22 g
2. Product for experiment: the nutritional compositions of Examples 1 to 7 of the present disclosure and rice.
3. Experiment Method:
80 mice of 18-22 g, half of them being male and half of them being female, were randomly divided into 8 groups according to sex and body weight, respectively being a control group, and seven test groups (Examples 1 to 7). Except the control group, the mice of all the other groups were administrated by gavage with the corresponding nutritional compositions of Examples 1 to 7 by 2 g/kg each time, three times a day for 20 d continuously, and the control group was administrated by gavage with an equal amount of rice. The administration by gavage was continued for 20 d, and 1 h after the last time of administration by gavage, the mice were subjected to intraperitoneal injection of 50 mg/kg of pentobarbital sodium, to observe the time that the righting reflex of the mice disappeared and restored and record the sleep duration for 2 h in total, wherein the sleep duration was recorded as 2 h when it exceeded 2 h. Experiment results are shown in Table 3.

TABLE 3

Experiment Results of Influence on Sleeping Time of Mice

| Group | Number of Animal | Sleeping Time/min |
|---|---|---|
| Control Group | 10 | 63 ± 11.7 |
| Example 1 | 10 | 85 ± 12.4** |
| Example 2 | 10 | 93 ± 18.5** |
| Example 3 | 10 | 102 ± 13.8** |
| Example 4 | 10 | 89 ± 19.4** |
| Example 5 | 10 | 105 ± 21.8** |
| Example 6 | 10 | 97 ± 18.8** |
| Example 7 | 10 | 107 ± 16.8** |

Compared with the control group,
**$P < 0.01$.

The results indicate that the nutritional compositions of the present disclosure can significantly increase the sleeping time of the mice, and Examples 1 to 7 have extremely significant differences from the control group ($P<0.01$). Thus, the nutritional compositions of the present disclosure have stronger hypnosis and tranquillizing effect than common rice.

The descriptions above are only preferred examples of the present invention, which are not used to limit the present invention. For a person skilled in the art, the present invention may have various changes and variations. Any modifications, equivalent substitutions, improvements etc. within the spirit and principle of the present invention shall all be included in the scope of protection of the present invention.

What is claimed is:

1. A nutritional composition for nourishing heart, comprising the following raw material components and proportions thereof, in parts by weight (pbw): rice 58-83 pbw, red beans 7-25 pbw, lotus seeds 5-16 pbw, Lilium brownii 2-7 pbw, and longan 0.4-1.6 pbw, wherein the composition is a composition prepared by the process comprising the following sequential steps:
   step 1, preparing raw materials: purifying and sorting rice, red beans lotus seeds, Lilium brownii, and longan for subsequent use;
   step 2, frying: frying the prepared raw materials under a condition of 100-200° C. for 25-120 min;
   step 3, dosing: grinding the fried raw materials, then mixing and stirring evenly the ground materials according to the proportions to obtain a rice powder;
   step 4, granulating: extruding the rice powder obtained in step 3 through a double-screw extruder, followed by gelatinization and granulation thereof, to obtain mixed rice grains;
   step 5, drying: drying the mixed rice grains through a microwave dryer, wherein a water content of the material is kept below 12%, and cooling the dried mixed rice grains at room temperature; and
   step 6, sieving and packaging: sieving the cooled mixed rice grains, and optionally vacuum-packaging the sieved mixed rice grains, thereby obtaining the heart-nourishing nutritional composition.

2. The nutritional composition for nourishing heart of claim 1, comprising rice 65-75 pbw, red beans 11-18 pbw, lotus seeds 8-13 pbw, Lilium brownii 3-5 pbw, and longan 0.7-1.2 pbw.

3. The nutritional composition for nourishing heart of claim 2, further comprising a Chinese herbal medicine extract of 1-3 parts, wherein the Chinese herbal medicine extract comprises comprises the following components of raw materials in parts by weight (pbw): 12-30 pbw mulberry, 5-15 pbw ginkgo, 15-20 pbw Gordon euryale seeds, 14-23 pbw Chinese yam, 13-25 pbw semen Sesami nigrum, and 7-17 pbw orange peels.

4. The nutritional composition for nourishing heart of claim 1, comprising rice 70 pbw, red beans 15 pbw, lotus seeds 10 pbw, Lilium brownii 4 pbw, and longan 1 pbw.

5. The nutritional composition for nourishing heart of claim 4, further comprising a Chinese herbal medicine extract of 1-3 parts, wherein the Chinese herbal medicine extract comprises the following components of raw materials in parts by weight (pbw): 12-30 pbw mulberry, 5-15 pbw ginkgo, 15-20 pbw Gordon euryale seeds, 14-23 pbw Chinese yam, 13-25 pbw semen Sesami nigrum, and 7-17 pbw orange peels.

6. The nutritional composition for nourishing heart of claim 1, further comprising a Chinese herbal medicine extract of 1-3 parts, wherein the Chinese herbal medicine extract comprises the following components of raw materials in parts by weight (pbw): 12-30 pbw mulberry, 5-15 pbw ginkgo, 15-20 pbw Gordon euryale seeds, 14-23 pbw Chinese yam, 13-25 parts by weight of semen Sesami nigrum, and 7-17 parts by weight of orange peels.

7. A method for preparing a nutritional composition for nourishing heart of claim 1, wherein the method comprises the following steps in sequence:
   step 1, preparing raw materials: purifying by removing impurities therefrom and sorting rice, red beans, lotus seeds, Lilium brownii, and longan for subsequent use;
   step 2, frying: frying the prepared raw materials under a condition of 100-200° C. for 25-120 min;
   step 3, dosing: grinding the fried raw materials, then mixing and stirring evenly the ground materials according to proportions sufficient to obtain a rice powder;
   step 4, granulating: extruding the rice powder obtained in step 3 through a double-screw extruder, followed by gelatinization and granulation thereof, to obtain mixed rice grains;
   step 5, drying: drying the mixed rice grains through a microwave dryer, wherein a water content of the material is kept below 12%, and cooling the dried mixed rice grains at room temperature; and
   step 6, sieving and packaging: sieving the cooled mixed rice grains, and optionally vacuum-packaging the sieved mixed rice grains, thereby obtaining the heart-nourishing nutritional composition.

8. The method for preparing a nutritional composition for nourishing heart of claim 7, wherein temperatures of three phases of the double-screw extruder are maintained at 60° C., 90-120° C., and 90° C., respectively.

9. The method for preparing a nutritional composition for nourishing heart of claim 7, wherein a heating temperature of the microwave dryer is maintained at 50-60° C.

10. The method for preparing a nutritional composition for nourishing heart of claim 7, wherein in a dosing process of the step 3, 1-3 parts of a Chinese herbal medicine extract is further added, and the Chinese herbal medicine extract comprises: 12-30 pbw mulberry, 5-15 pbw ginkgo, 15-20 pbw Gordon euryale seeds, 14-23 pbw Chinese yam, 13-25 pbw semen Sesami nigrum, and 7-17 pbw orange peels.

11. The method for preparing a nutritional composition for nourishing heart of claim 10, wherein the Chinese herbal medicine extract is prepared by:
   drying and grinding respective raw materials into a medicinal powder, and subjecting the medicinal powder to ultrasonic extraction, centrifugation, and concentration with an ethanol solution of 40-65% in volume percentage, thereby obtaining the Chinese herbal medicine extract.

12. The method for preparing a nutritional composition for nourishing heart of claim 11, wherein in the process of preparing the Chinese herbal medicine extract, a vacuum dryer is used for drying, with a temperature of 75° C. to 80° C. and a vacuum negative pressure of from 0.08 MPa to a vacuum negative pressure of 0.1 MPa.

13. A method for preparing a nutritional composition for nourishing heart of claim 2, wherein the method comprises the following steps in sequence:
   step 1, preparing raw materials: purifying by removing impurities therefrom and sorting rice, red beans, lotus seeds, Lilium brownii, and longan for subsequent use;
   step 2, frying: frying the prepared raw materials under a condition of 100-200° C. for 25-120 min;
   step 3, dosing: grinding the fried raw materials, then mixing and stirring evenly the ground materials according to proportions sufficient to obtain a rice powder;
   step 4, granulating: extruding the rice powder obtained in step 3 through a double-screw extruder, followed by gelatinization and granulation thereof, to obtain mixed rice grains;
   step 5, drying: drying the mixed rice grains through a microwave dryer, wherein a water content of the material is kept below 12%, and cooling the dried mixed rice grains at room temperature; and
   step 6, sieving and packaging: sieving the cooled mixed rice grains, and optionally vacuum-packaging the sieved mixed rice grains, thereby obtaining the heart-nourishing nutritional composition.

14. The method for preparing a nutritional composition for nourishing heart of claim 13, wherein temperatures of three phases of the double-screw extruder are kept at 60° C., 90-120° C., and 90° C., respectively.

15. The method for preparing a nutritional composition for nourishing heart of claim 13, wherein a heating temperature of the microwave dryer is maintained at 50-60° C.

16. The method for preparing a nutritional composition for nourishing heart of claim 13, wherein in a dosing process of the step 3, 1-3 parts of a Chinese herbal medicine extract is further added, and the Chinese herbal medicine extract comprises: 12-30 pbw mulberry, 5-15 pbw ginkgo, 15-20 pbw Gordon euryale seeds, 14-23 pbw Chinese yam, 13-25 pbw semen Sesami *nigrum*, and 7-17 pbw orange peels.

17. The method for preparing a nutritional composition for nourishing heart of claim 16, wherein the Chinese herbal medicine extract is prepared by:
    drying and grinding respective raw materials into a medicinal powder, and subjecting the medicinal powder to ultrasonic extraction, centrifugation, and concentration with an ethanol solution of 40-65% in volume percentage, thereby obtaining the Chinese herbal medicine extract.

18. The method for preparing a nutritional composition for nourishing heart of claim 17, wherein in the process of preparing the Chinese herbal medicine extract, a vacuum dryer is used for drying, the vacuum dryer providing a temperature of 75° C. to 80° C. and a vacuum negative pressure of from 0.08 MPa to a vacuum negative pressure of 0.1 MPa.

19. A method for preparing a nutritional composition for nourishing heart of claim 2, wherein the method comprises the following steps in sequence:
    step 1, preparing raw materials: purifying by removing impurities therefrom and sorting rice, red beans, lotus seeds, *Lilium brownii*, and longan for subsequent use;
    step 2, frying: frying the prepared raw materials under a condition of 100-200° C. for 25-120 min;
    step 3, dosing: grinding the fried raw materials, then mixing and stirring evenly the ground materials according to proportions sufficient to obtain a rice powder;
    step 4, granulating: extruding the rice powder obtained in step 3 through a double-screw extruder, followed by gelatinization and granulation thereof, to obtain mixed rice grains;
    step 5, drying: drying the mixed rice grains through a microwave dryer, wherein a water content of the material is kept below 12%, and cooling the dried mixed rice grains at room temperature; and
    step 6, sieving and packaging: sieving the cooled mixed rice grains, and optionally vacuum-packaging the sieved mixed rice grains, thereby obtaining the heart-nourishing nutritional composition.

20. The method for preparing a nutritional composition for nourishing heart of claim 19, wherein temperatures of three phases of the double-screw extruder are maintained at 60° C., 90-120° C., and 90° C., respectively.

* * * * *